(12) United States Patent
Hasegawa et al.

(10) Patent No.: US 6,403,823 B2
(45) Date of Patent: Jun. 11, 2002

(54) ESTER COMPOUNDS HAVING ALICYCLIC STRUCTURE AND METHOD FOR PREPARING SAME

(75) Inventors: Koji Hasegawa; Takeru Watanabe; Takeshi Kinsho; Mutsuo Nakashima; Seiichiro Tachibana; Tsunehiro Nishi; Jun Hatakeyama, all of Nakakubiki-gun (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 09/842,006

(22) Filed: Apr. 26, 2001

(30) Foreign Application Priority Data

Apr. 28, 2000 (JP) .......................... 2000-131164

(51) Int. Cl.$^7$ .............................................. C07C 69/74
(52) U.S. Cl. ........................................ 560/116; 560/128
(58) Field of Search .................. 560/128, 116

(56) References Cited

U.S. PATENT DOCUMENTS 6,063,542 A * 5/2000 Hyeon et al.
6,146,810 A * 11/2000 Seo et al.
6,268,106 B1 * 7/2001 Park et al.

\* cited by examiner

Primary Examiner—Gary Geist
Assistant Examiner—Hector Reyes
(74) Attorney, Agent, or Firm—Millen, White, Zelano & Branigan, P.C.

(57) ABSTRACT

Ester compounds of formula (1) are useful as monomers to form base resins for use in chemically amplified resist compositions adapted for micropatterning lithography.

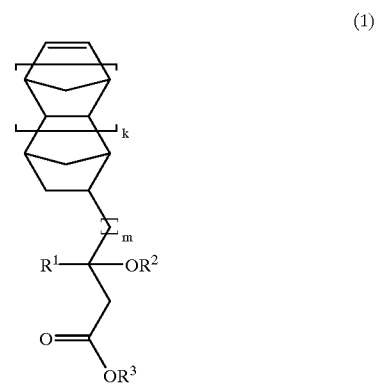

(1)

$R^1$ is H or $C_{1-6}$ alkyl, $R^2$ is an unsubstituted or halo-substituted acyl or alkoxycarbonyl group of 1–15 carbon atoms, $R^3$ is an acid labile group, k is 0 or 1, and m is an integer from 0 to 5.

15 Claims, No Drawings

ESTER COMPOUNDS HAVING ALICYCLIC STRUCTURE AND METHOD FOR PREPARING SAME

This invention relates to novel ester compounds useful as monomers to form base resins for use in chemically amplified resist compositions adapted for micropatterning lithography, and a method for preparing the same.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel ester compound useful as a monomer to form a polymer for use in the formulation of a photoresist composition which exhibits a high reactivity and transparency when processed by photolithography using light with a wavelength of less than 300 nm, especially ArF excimer laser light as the light source. Another object is to provide a method for preparing the ester compound.

The inventor has found that an ester compound of formula (1) can be prepared in high yields by a simple method, that a polymer obtained from this ester compound has high transparency at the exposure wavelength of an excimer laser, and that a resist composition comprising the polymer as a base resin is improved in sensitivity and resolution.

The invention provides an ester compound of the following general formula (1).

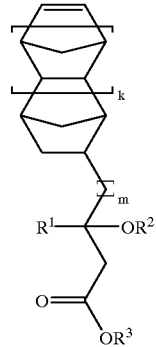

(1)

Herein $R^1$ is hydrogen or a straight, branched or cyclic alkyl group of 1 to 6 carbon atoms, $R^2$ is an acyl or alkoxycarbonyl group of 1 to 15 carbon atoms in which some or all of the hydrogen atoms on the constituent carbon atoms may be substituted with halogen atoms, $R^3$ is an acid labile group, k is 0 or 1, and m is an integer from 0 to 5.

Preferably the ester compound has the following general formula (2) or (3).

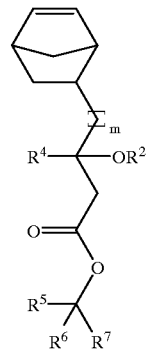

(2)

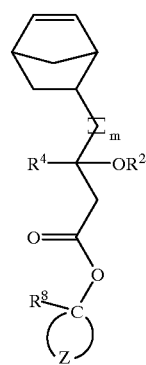

(3)

Herein m and $R^2$ are as defined above, $R^4$ is hydrogen or methyl, $R^5$ to $R^8$ are independently selected from straight, branched or cyclic alkyl groups of 1 to 15 carbon atoms, the sum of carbon atoms in $R^5$, $R^6$ and $R^7$ is at least 4, and Z is a divalent hydrocarbon group of 4 to 15 carbon atoms which forms a ring with the carbon atom to which it is connected at opposite ends.

A method for preparing the ester compound forms another aspect of the invention, which involves the steps of effecting addition reaction of a metal enolate of acetate of the following formula (5) to a carbonyl compound of the following formula (4) to form a β-hydroxyester compound of the following formula (6), and effecting acylation or alkoxycarbonylation of the hydroxyl group of the β-hydroxyester compound.

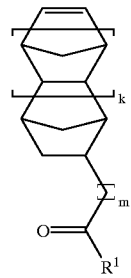

(4)

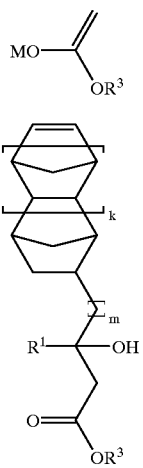

(5)

(6)

Herein k, m, $R^1$ and $R^3$ are as defined above, M is Li, Na, K, MgY or ZnY, and Y is a halogen atom.

DESCRIPTION OF THE PREFERRED EMBODIMENT

The ester compounds of the invention are of the following general formula (1).

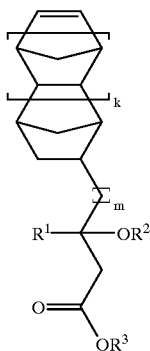

(1)

Herein $R^1$ is hydrogen or a straight, branched or cyclic alkyl group of 1 to 6 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl. $R^2$ is an acyl or alkoxycarbonyl group of 1 to 15 carbon atoms in which some or all of the hydrogen atoms on the constituent carbon atoms may be substituted with halogen atoms. Exemplary of $R^2$ are formyl, acetyl, ethylcarbonyl, pivaloyl, methoxycarbonyl, ethoxycarbonyl, tert-butoxycarbonyl, trifluoroacetyl, trichloroacetyl, and 2,2,2-trifluoroethylcarbonyl. $R^3$ is an acid labile group. The letter k is 0 or 1, and m is an integer from 0 to 5 (i.e., $0 \leq m \leq 5$), and preferably from 0 to 3.

The preferred acid labile group represented by $R^3$ are those of the following formulas.

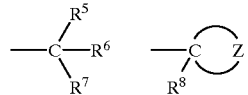

$R^5$ to $R^8$ and Z are as defined below.

Preferred among the ester compounds of formula (1) are ester compounds of the following general formula (2) or (3).

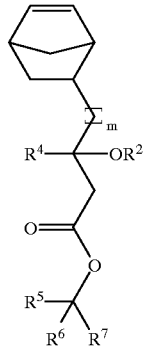

(2)

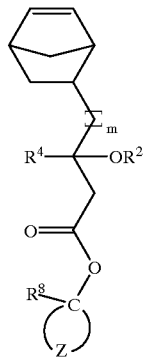

(3)

Herein m and $R^2$ are as defined above. $R^4$ is hydrogen or methyl. $R^5$ to $R^8$ are independently selected from straight, branched or cyclic alkyl groups of 1 to 15 carbon atoms. The total number of carbon atoms in $R^5$, $R^6$ and $R^7$ is at least 4. Examples of the straight, branched or cyclic alkyl groups of 1 to 15 carbon atoms include methyl, ethyl, n-propyl, isopropyl, n-butyl, isobutyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, bicyclo[2.2.1]heptyl, bicyclo[2.2.2]octyl, bicyclo[3.3.1]nonyl, bicyclo[4.4.0]decanyl, tricyclo[5.2.1.0$^{2,6}$]decanyl, tetracyclo[4.4.0.1$^{2,5}$.1$^{7,10}$]dodecanyl, and adamantyl. Z stands for divalent hydrocarbon groups of 4 to 15 carbon atoms, such as alkylene and alkenylene groups, which each forms a ring with the carbon atom to which it is connected at opposite ends. Examples of the rings that Z forms include cyclopentane, cyclopentene, cyclohexane, cyclohexene, bicyclo[2.2.1]heptane, bicyclo[4.4.0]decane, tricyclo[5.2.1.0$^{2,6}$]decane, tetracyclo[4.4.0.1$^{2,5}$.1$^{7,10}$]-dodecane, and adamantane.

Illustrative, non-limiting, examples of the ester compounds of formula (1) and formulas (2) and (3) are given below.

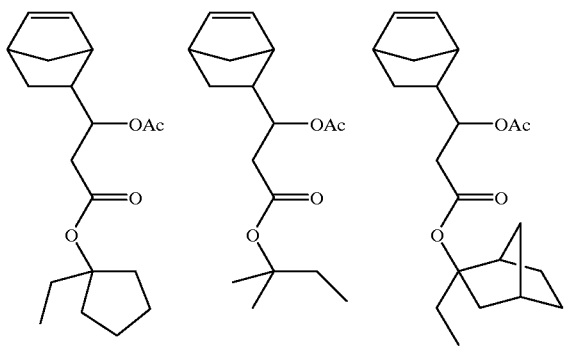
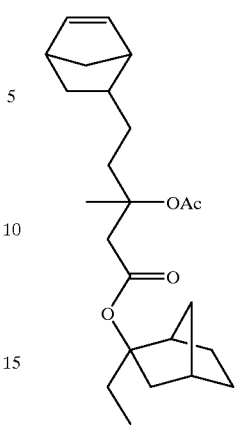
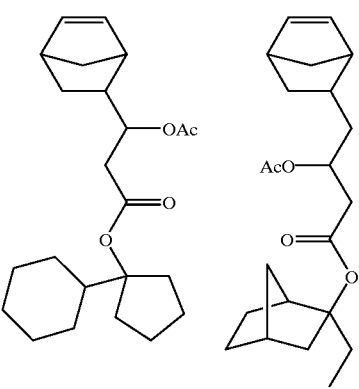
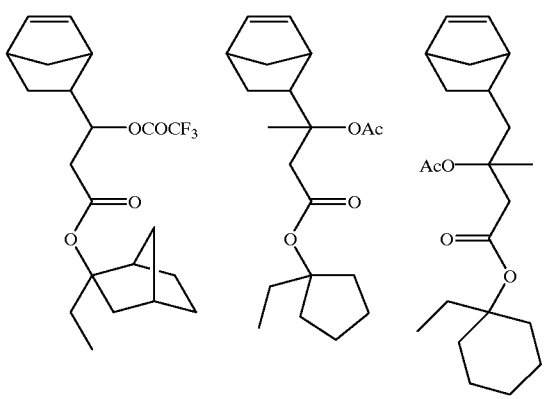
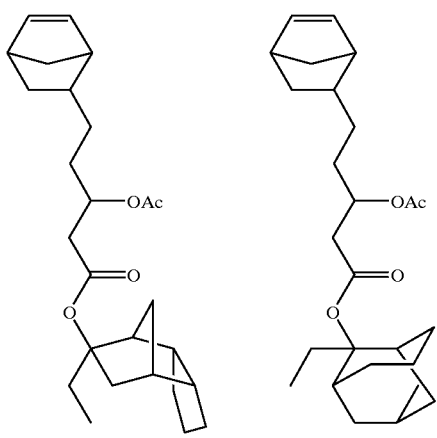

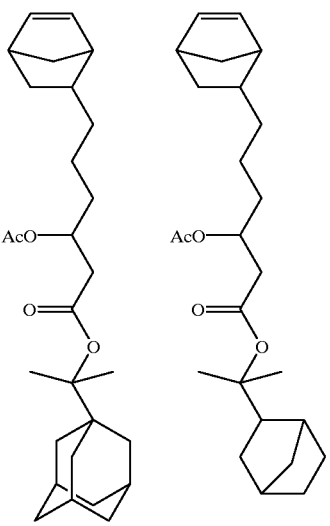
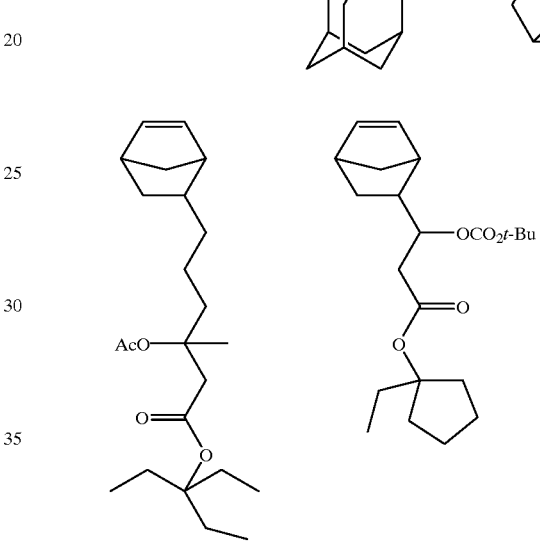
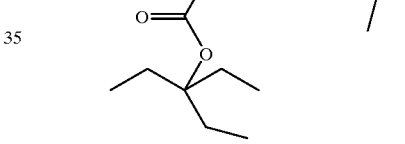

As seen from the reaction scheme shown below, the ester compound of formula (1) can be prepared by the first step of causing a base to act on a corresponding acetate of formula (7) (where X is hydrogen) or a corresponding haloacetate of formula (7) (where X is halogen) to form a metal enolate of formula (5) and effecting nucleophilic addition reaction of the metal enolate to a carbonyl compound of formula (4) to form a β-hydroxyester compound of formula (6), and the second step of effecting acylation or alkoxycarbonylation (or esterification) of the hydroxyl group on the β-hydroxester compound.

1st step

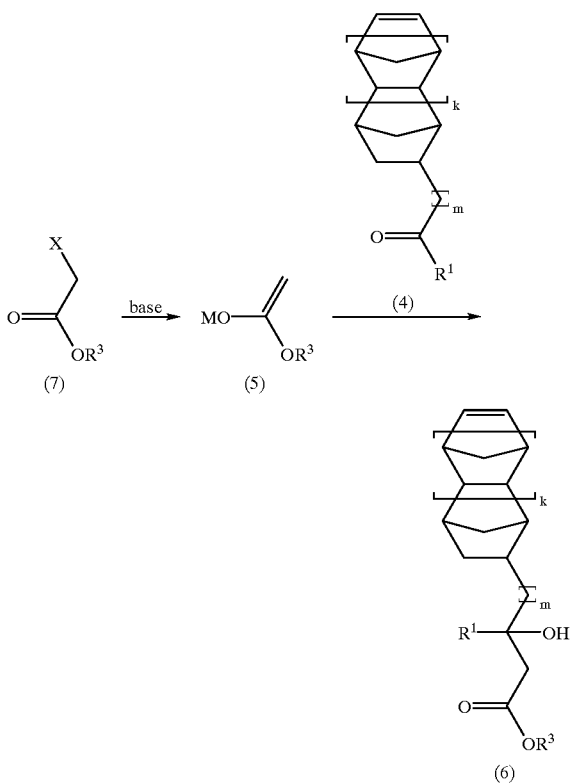

2nd step

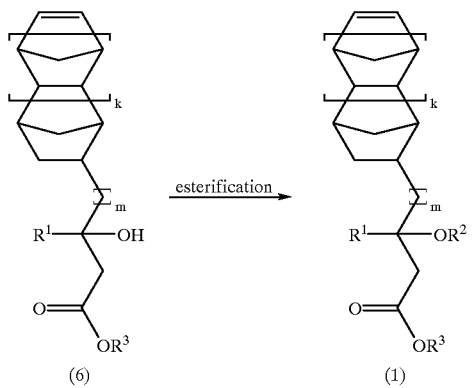

Herein, k, m, $R^1$, $R^2$ and $R^3$ are as defined above. X is hydrogen or halogen. M is Li, Na, K, MgY or ZnY, and Y is halogen.

In the first step, a base acts on a corresponding acetate (where X is hydrogen) or a corresponding haloacetate (where X is halogen) to form a metal enolate, and nucleophilic addition reaction is effected between the metal enolate and a carbonyl compound to form a β-hydroxyester compound. The bases used herein include metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and bromomagnesium diisopropylamide; alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate and potassium carbonate; metal hydrides such as boranes, alkylboranes, sodium hydride, lithium hydride, potassium hydride, and calcium hydride; alkyl metal compounds such as trityl lithium, trityl sodium, trityl potassium, methyl lithium, phenyl lithium, sec-butyl lithium, tert-butyl lithium, and ethyl magnesium bromide; and metals such as lithium, sodium, potassium, magnesium, and zinc, but are not limited thereto. It is noted that reaction using haloacetate and zinc is known as Reformatsky reaction.

In the addition reaction of the carbonyl compound of formula (4) with the metal enolate of formula (5), 0.8 to 1.5 mol of the metal enolate is preferably used per mol of the carbonyl compound. Useful solvents are ethers such as tetrahydrofuran, diethyl ether, di-n-butyl ether, 1,4-dioxane, ethylene glycol dimethyl ether, and ethylene glycol diethyl ether and hydrocarbons such as hexane, heptane, benzene, toluene, xylene and cumene, alone or in admixture thereof. The reaction temperature and time vary with particular starting reactants used. In one example where an acetate of formula (7) wherein X is hydrogen and a strong base such as lithium diisopropylamide or lithium bistrimethylsilylamide are used, the preferred reaction conditions include a reaction temperature in the low range of −80° C. to −30° C. and a reaction time of about ½ to about 3 hours because the metal enolate is thermally unstable. In another example where a haloacetate of formula (7) wherein X is halogen and a metal such as zinc or magnesium are used, it is generally preferred to keep the reaction temperature in the range of 20 to 80° C. and the reaction time in the range of about 1 to 20 hours. The reaction conditions are not limited to these ranges.

The second step is to esterify the alcoholic hydroxyl group produced in the first step. The reaction readily proceeds under well-known conditions. Preferably in a solventless system or in a solvent such as methylene chloride, toluene or hexane, the β-hydroxyester compound resulting from the first step, a corresponding acid anhydride such as acetic anhydride or trifluoroacetic anhydride, and a base such as triethylamine, pyridine or 4-dimethylaminopyridine are sequentially or simultaneously added while heating or cooling the system if necessary.

A polymer is prepared using the inventive ester compound as a monomer. The method is generally by mixing the monomer with a solvent, adding a catalyst or polymerization initiator, and effecting polymerization reaction while heating or cooling the system if necessary. This polymerization reaction can be effected in a conventional way.

A resist composition is formulated using as a base resin the polymer resulting from polymerization of the ester compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive ester compound lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Ester compounds within the scope of the invention were synthesized in accordance with the following formulation.

Synthesis Example 1
Synthesis of 1-Ethylcyclopentyl 3-Acetoxy-3-(5-norbornen-2-yl)propionate (Monomer 1)

First, in a nitrogen atmosphere, 184 g of lithium bis(trimethylsilyl)amide and 172 g of 1-ethylcyclopentyl acetate were reacted in 1 kg of dry tetrahydrofuran at −60° C. to form lithium enolate. Then 122 g of 5-norbornene-2-carbaldehyde was slowly added, following which the temperature was raised to −20° C. over one hour, at which reaction was effected. Then 1 kg of a saturated ammonium chloride aqueous solution was added to stop the reaction, whereupon hexane was: added for extraction. The organic layer was washed with water, dried over anhydrous sodium sulfate, filtered, and concentrated in vacuum, obtaining an alcohol intermediate. In 127 g of pyridine in the presence of 6 g of 4-dimethylaminopyridine, the alcohol intermediate was reacted with 123 g of acetic anhydride at 25° C. for 10 hours. Water, 30 g, was added to stop the reaction whereupon hexane was added for extraction. The organic layer was washed with water, dried over anhydrous sodium sulfate, filtered, concentrated in vacuum, and purified by silica gel column chromatography, obtaining 295 g (yield 92%) of 1-ethylcyclopentyl 3-acetoxy-3-(5-norbornen-2-yl)propionate, designated Monomer 1.

IR (thin film): ν=3059, 2968, 2872, 1740, 1371, 1340, 1238, 1157, 1026, 953 cm$^{-1}$ $^1$H-NMR of main diastereomer (270 MHz in CDCl$_3$): δ=0.58 (1H, ddd, J=11.7, 4.9, 2.4 Hz), 0.82 (3H, t, J=5.4 Hz), 1.10–2.15 {(16H, m) including 2.04 (3H, s)}, 2.36 (1H, dd, J=15.1, 7.3 Hz), 2.52 (1H, dd, J=15.1, 3.8 Hz), 2.61 (1H, m), 2.75–2.85 (2H, m), 4.60 (1H, ddd, J=10.7, 7.3, 3.8 Hz), 5.94 (1H, m), 6.18 (1H, m).

Synthesis Example 2
Synthesis of 2-Methyl-2-butyl 3-Acetoxy-3-(5-norbornen-2-yl)propionate (Monomer 2)

By following the procedure of Synthesis Example 1 except that 2-methyl-2-butyl acetate was used instead of 1-ethylcyclopentyl acetate, there was obtained 2-methyl-2-butyl 3-acetoxy-3-(5-norbornen-2-yl)propionate. Yield 93%.

Synthesis Example 3
Synthesis of 2-Ethyl-2-exo-norbornyl 3-Acetoxy-3-(5-norbornen-2-yl)propionate (Monomer 3)

By following the procedure of Synthesis Example 1 except that 2-ethyl-2-exo-norbornyl acetate was used instead of 1-ethylcyclopentyl acetate, there was obtained 2-ethyl-2-exo-norbornyl 3-acetoxy-3-(5-norbornen-2-yl)propionate. Yield 91%.

IR (thin film): ν=3057, 2966, 2872, 1740, 1371, 1332, 1288, 1238, 1174, 1159, 1132, 1026, 951 cm$^{-1}$ $^1$H-NMR of main diastereomer (270 MHz in CDCl$_3$): δ=0.58 (1H, ddd, J=11.2, 4.9, 2.4 Hz), 0.79 (3H, t, J=7.3 Hz), 0.95–2.00 (12H, m), 2.04 (3H, s), 2.10–2.70 (6H, m), 2.75–2.85 (2H, m), 4.60 (1H, m), 5.94 (1H, m), 6.16 (1H, m).

Synthesis Example 4
Synthesis of 1-Cyclohexylcyclopentyl 3-Acetoxy-3-(5-norbornen-2-yl)propionate (Monomer 4)

By following the procedure of Synthesis Example 1 except that 1-cyclohexylcyclopentyl acetate was used instead of 1-ethylcyclopentyl acetate, there was obtained 1-cyclohexylcyclopentyl 3-acetoxy-3-(5-norbornen-2-yl)propionate. Yield 90%.

IR (thin film): ν=3057, 2933, 2854, 1741, 1448, 1371, 1338, 1238, 1155, 1147, 1024 cm$^{-1}$ $^1$H-NMR of main diastereomer (300 MHz in CDCl$_3$): δ=0.58 (1H, ddd, J=11.6, 4.7, 2.5 Hz), 0.90–2.00 (21H, m), 2.04 (3H, s), 2.25–2.70 {(4H, m) including 2.36 (1H, dd, J=15.1, 7.4 Hz), 2.51 (1H, dd, J=15.1, 3.6 Hz)}, 2.75–2.85 (2H, m), 4.61 (1H, m), 5.95 (1H, m), 6.18 (1H, m).

Synthesis Example 5
Synthesis of 2-Ethyl-2-exo-norbornyl 3-Acetoxy-4-(5-norbornen-2-yl)butyrate (Monomer 5)

By following the procedure of Synthesis Example 3 except that 2-(5-norbornen-2-yl)acetoaldehyde was used instead of 5-norbornene-2-carbaldehyde, there was obtained 2-ethyl-2-exo-norbornyl 3-acetoxy-4-(5-norbornen-2-yl)butyrate. Yield 90%.

IR (thin film): ν=3057, 2966, 2872, 1741, 1458, 1441, 1373, 1240, 1192, 1171, 1132, 1025 cm$^{-1}$ $^1$H-NMR of main diastereomer (300 MHz in CDCl$_3$): δ=0.56 (1H, m), 0.79 (3H, t, J=7.3 Hz), 1.00–2.10 ((18H, m) including 2.02 (3H, s)), 2.10–2.30 (2H, m), 2.40–2.60 (3H, m), 2.70–2.85 (2H, m), 5.20 (1H, m), 5.92 (1H, m), 6.11 (1H, m).

Synthesis Example 6
Synthesis of 2-Ethyl-2-exo-norbornyl 3-(5-Norbornen-2-yl)-3-trifluoroacetoxypropionate (Monomer 6)

By following the procedure of Synthesis Example 1 except that trifluoroacetic anhydride was used instead of acetic anhydride, there was obtained 2-ethyl-2-exo-norbornyl 3-(5-norbornen-2-yl)-3-trifluoroacetoxypropionate. Yield 85%.

IR (thin film): ν=3061, 2970, 2875, 1786, 1730, 1383, 1358, 1265, 1221, 1167 cm$^{-1}$ $^1$H-NMR of main diastereomer (300 MHz in CDCl$_3$): δ=0.60 (1H, m), 0.77 (3H, t, J=6.8 Hz), 0.95–2.00 (12H, m), 2.10–2.25 (2H, m), 2.30–2.90 (6H, m), 4.87 (1H, m), 5.96 (1H, m), 6.23 (1H, m).

Synthesis Example 7
Synthesis of 1-Ethylcyclopentyl 3-Acetoxy-3-(5-norbornen-2-yl)butyrate (Monomer 7)

By following the procedure of Synthesis Example 1 except that 5-acetyl-2-norbornene was used instead of 5-norbornene-2-carbaldehyde, there was obtained 1-ethylcyclopentyl 3-acetoxy-3-(5-norbornen-2-yl)butyrate. Yield 80%.

Synthesis Example 8
Synthesis of 1-Ethylcyclohexyl 3-Acetoxy-3-methyl-4-(5-norbornen-2-yl)butyrate (Monomer 8)

The procedure of Synthesis Example 1 was repeated except that 1-ethylcyclohexyl acetate was used instead of 1-ethylcyclopentyl acetate, and 3-(5-norbornen-2-yl)acetone was used instead of 5-norbornene-2-carbaldehyde. There was obtained 1-ethylcyclohexyl 3-acetoxy-3-methyl-4-(5-norbornen-2-yl)butyrate. Yield 81%.

Synthesis Example 9
Synthesis of 8-Ethyl-8-exo-tricyclo[5.2.1.0$^{2,6}$]decanyl 3-Acetoxy-5-(5-norbornen-2-yl)valerate (Monomer 9)

The procedure of Synthesis Example 1 was repeated except that 8-ethyl-8-exo-tricyclo[5.2.1.0$^{2,6}$]decanyl acetate was used instead of 1-ethylcyclopentyl acetate, and 3-(5-norbornen-2-yl)propionaldehyde was used instead of 5-norbornene-2-carbaldehyde. There was obtained 8-ethyl-8-exo-tricyclo[5.2.1.0$^{2,6}$]decanyl 3-acetoxy-5-(5-norbornen-2-yl)valerate. Yield 89%.

Synthesis Example 10
Synthesis of 2-Ethyl-2-adamantyl 3-Acetoxy-5-(5-norbornen-2-yl)valerate (Monomer 10)

The procedure of Synthesis Example 9 was repeated except that 2-ethyl-2-adamantyl acetate was used instead of 8-ethyl-8-exo-tricyclo[5.2.1.0$^{2,6}$]decanyl acetate. There was obtained 2-ethyl-2-adamantyl 3-acetoxy-5-(5-norbornen-2-yl)valerate. Yield 91%.

Synthesis Example 11
Synthesis of 2-Ethyl-2-exo-norbornyl 3-Acetoxy-3-methyl-5-(5-norbornen-2-yl)valerate (Monomer 11)

The procedure of Synthesis Example 3 was repeated except that 4-(5-norbornen-2-yl)butanone was used instead of 5-norbornene-2-carbaldehyde. There was obtained 2-ethyl-2-exo-norbornyl 3-acetoxy-3-methyl-5-(5-norbornen-2-yl)-valerate. Yield 81%.

Synthesis Example 12
Synthesis of 2-(1-Adamantyl)-2-propyl 3-Acetoxy-6-(5-norbornen-2-yl)hexanoate (Monomer 12)

The procedure of Synthesis Example 1 was repeated except that 2-(1-adamantyl)-2-propyl acetate was used instead of 1-ethylcyclopentyl acetate, and 4-(5-norbornen-2-yl)butyrylaldehyde was used instead of 5-norbornene-2-carbaldehyde. There ,was obtained 2-(1-adamantyl)-2-propyl 3-acetoxy-6-(5-norbornen-2-yl)hexanoate. Yield 90%.

Synthesis Example 13
Synthesis of 2-(2-Norbornyl)-2-propyl 3-Acetoxy-6-(5-norbornen-2-yl)hexanoate (Monomer 13)

The procedure of Synthesis Example 12 was repeated except that 2-(2-norbornyl)-2-propyl acetate was used instead of 2-(1-adamantyl)-2-propyl acetate. There was obtained 2-(2-norbornyl)-2-propyl 3-acetoxy-6-(5-norbornen-2-yl)hexanoate. Yield 91%.

Synthesis Example 14
Synthesis of 3-Ethyl-3-pentyl 3-Acetoxy-3-methyl-6-(5-norbornen-2-yl)hexanoate (Monomer 14)

The procedure of Synthesis Example 1 was repeated except that 3-ethyl-3-pentyl acetate was used instead of 1-ethylcyclopentyl acetate, and 5-(5-norbornen-2-yl)-2-pentanone was used instead of 5-norbornene-2-carbaldehyde. There was obtained 3-ethyl-3-pentyl 3-acetoxy-3-methyl-6-(5-norbornen-2-yl)hexanoate. Yield 83%.

Synthesis Example 15
Synthesis of 1-Ethylcyclopentyl 3-Acetoxy-3-(8-tetracyclo[4.4.0.1$^{2,5}$.1$^{7,10}$]dodecane-3-yl)propionate (Monomer 15)

The procedure of Synthesis Example 1 was repeated except that 8-tetracyclo[4.4.0.1$^{2,5}$.1$^{7,10}$]dodecene-3-carbaldehyde was used instead of 5-norbornene-2-carbaldehyde. There was obtained 1-ethylcyclopentyl 3-acetoxy-3-(8-tetracyclo[4.4.0.1$^{2,5}$.1$^{7,10}$]dodecane-3-yl)propionate. Yield 92%.

Synthesis Example 16

Synthesis of 1-Ethylcyclopentyl 3-Tert-butoxycarbonyloxy-3-(5-norbornen-2-yl)propionate (Monomer 16)

The procedure of Synthesis Example 1 was repeated except that di-tert-butyl pyrocarbonate was used instead of acetic anhydride. There was obtained 1-ethylcyclopentyl 3-tert-butoxycarbonyloxy-3-(5-norbornen-2-yl)propionate. Yield 85%.

The structural formulas of Monomers 1 to 16 are shown below.

Monomer 1

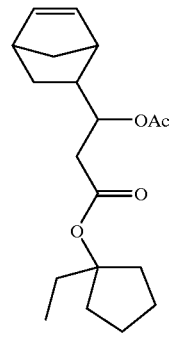

Monomer 2

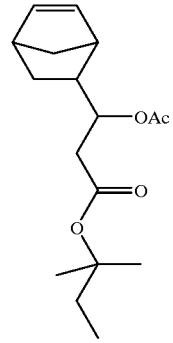

Monomer 3

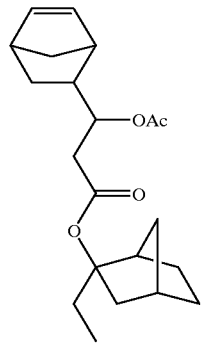

-continued
Monomer 4
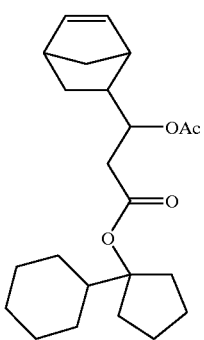
Monomer 5
Monomer 6
Monomer 7
-continued
Monomer 8
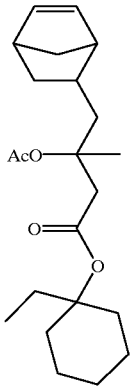
Monomer 9
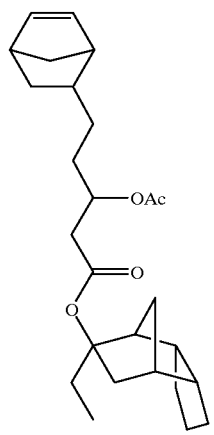
Monomer 10
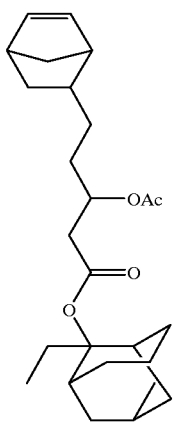
Monomer 11
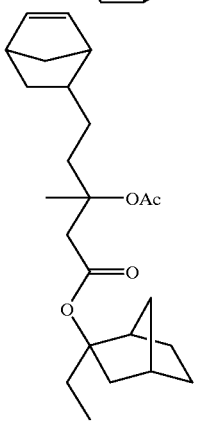

Monomer 12

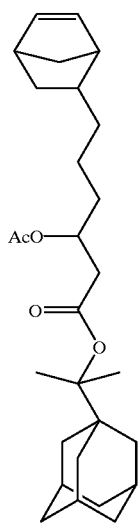

Monomer 13

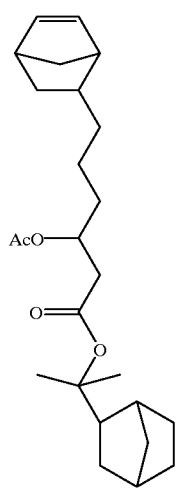

Monomer 14

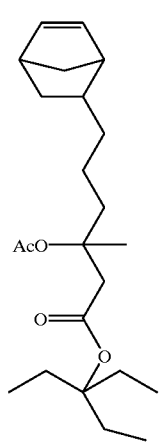

Monomer 15

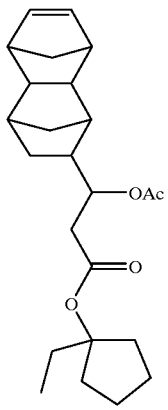

Monomer 16

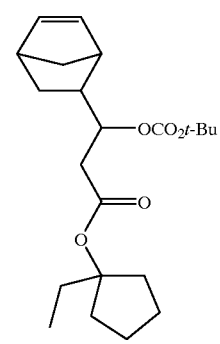

Reference Example

Polymers were synthesized using the ester compounds obtained in the above Synthesis Examples and examined for transparency.

Polymerization reaction was effected between Monomer 1 and maleic anhydride using the initiator V65 (by Wako Junyaku K.K.), yielding an alternating copolymer of 1-ethylcyclopentyl 3-acetoxy-3-(5-norbornen-2-yl)propionate/maleic anhydride. The polymer was measured for transmittance at a wavelength of 193 nm, finding 78.0% at a film thickness of 500 nm.

Comparative Reference Example

For comparison purposes, an alternating copolymer of tert-butyl 5-norbornene-2-carboxylate/maleic anhydride was measured for transmittance at a wavelength of 193 nm, finding 55.0% at a film thickness of 500 nm.

It was confirmed that polymers resulting from the inventive ester compounds have very high transparency as compared with prior art polymers.

Japanese Patent Application No. 2000-131164 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ester compound of the following general formula (1):

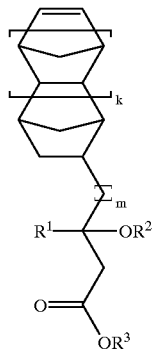

(1)

wherein $R^1$ is hydrogen or a straight, branched or cyclic alkyl group of 1 to 6 carbon atoms $R^2$ is an acyl or alkoxycarbonyl group of 1 to 15 carbon atoms in which some or all of the hydrogen atoms on the constituent carbon atoms may be substituted with halogen atoms, $R^3$ is an acid labile group, represented by

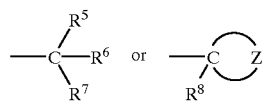

wherein $R^5$ to $R^8$ are independently selected from straight, branched or cyclic alkyl groups of 1 to 15 carbon atoms, the sum of carbon atoms in $R^5$, $R^6$ and $R^7$ is at least 5 and at least one of $R^5$ to $R^7$ is a cyclic alkyl group of 3 to 15 carbon atoms, and Z is a divalent hydrocarbon group of 4 to 15 carbon atoms which form a ring with the carbon atom to which it is connected at opposite ends, k is 0 or 1, and m is an integer from 0 to 5.

2. The ester compound of claim 1 having the following general formula (2) or (3):

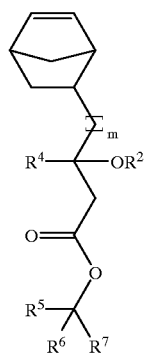

(2)

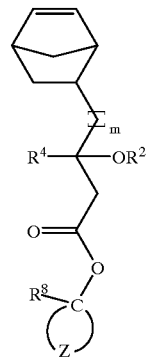

(3)

wherein m and $R^2$ are as defined above, $R^4$ is hydrogen or methyl, $R^5$ to $R^8$ are independently selected from straight, branched or cyclic alkyl groups of 1 to 15 carbon atoms, the sum of carbon atoms in $R^5$, $R^6$ and $R^7$ is at least 5, and at least one of $R^5$ to $R^7$ is a cyclic alkyl group of 3 to 15 carbon atoms, and Z is a divalent hydrocarbon group of 4 to 15 carbon atoms which forms a ring with the carbon atom to which it is connected at opposite ends.

3. A method for preparing the ester compound of claim 1, comprising the steps of effecting addition reaction of a metal enolate of acetate of the following formula (5) to a carbonyl compound of the following formula (4) to form a β-hydroxyester compound of the following formula (6), and effecting acylation or alkoxycarbonylation of the hydroxyl group on the β-hydroxyester compound,

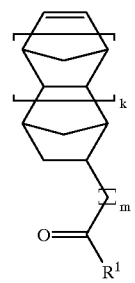

(4)

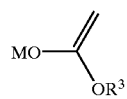

(5)

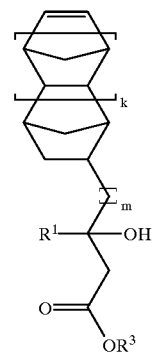

(6)

wherein k, m, $R^1$ and $R^3$ are as defined above, M is Li, Na, K or MgY, and Y is a halogen atom.

4. An ester compound according to claim 1, wherein the R$^1$ alkyl group is methyl, ethyl, n-propyl, isopropyl, n-butyl, isobutyl, sec-butyl, tert-butyl, tert-amyl, n-pentyl, n-hexyl, cyclopentyl, or cyclohexyl.

5. An ester compound according to claim 1, wherein R$^2$ group is formyl, acetyl, ethylcarbonyl, pivaloyl, methoxycarbonyl, ethoxycarbonyl, tert-butoxycarbonyl, trifluoroacetyl, trichloroacetyl, or 2,2,2,-trifluoroethylcarbonyl.

6. An ester compound according to claim 1, wherein m is an integer from 0 to 3.

7. An ester compound according to claim 2, wherein the straight, branched or cyclic alkyl groups of R$_5$ to R$_8$ include methyl, ethyl, n-propyl, isopropyl, n-butyl, isobutyl, sec-butyl, tert-butyl, tert-amyl, n-pentyl, n-hexyl, cyclopentyl, cyclohexyl, cyclopentylmethyl, cyclopentylethyl, cyclohexylmethyl, cyclohexylethyl, bicyclo[2.2.1]heptyl, bicyclo[2.2.2]octyl, bicyclo[3.3.1]nonyl, bicyclo[4.4.0]decanyl, tricyclo[5.2.1.0$^{2,6}$]decanyl, tetracyclo[4.4.0.1$^{2,5}$.1$^{7,10}$]dodecanyl, or adamantyl.

8. An ester compound according to claim 2, wherein the ring that Z forms is cyclopentane cyclopentene, cyclohexane, cyclohexene, bicyclo[2.2.1]heptane, bicyclo[4.4.0]decane, tricyclo[5.2.1.0$^{2,6}$]decane, tetracyclo[4.4.0.1$^{2,5}$.1$^{7,10}$]-dodecane, or adamantane.

9. A method according to claim 3 including a step wherein a base acts on a corresponding acetate or a corresponding haloacetate to form the metal enolate.

10. A method according to claim 3, wherein the addition reaction is conducted at a reaction temperature of –80° C. to –30° C. and a reaction time of about ½ to about 3 hours.

11. A method according to claim 3, wherein the addition reaction is conducted at a reaction temperature of 20 to 80° C. and a reaction time of about 1 to about 20 hours.

12. A method of preparing a polymer comprising mixing the monomer of claim 1 with a solvent, adding a catalyst or polymerization initiator, and effecting polymerization reaction while optionally heating or cooling the reactants.

13. An ester compound of the following general formula (1):

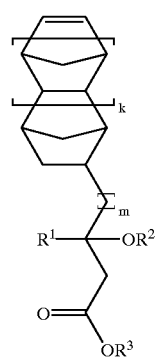

(1)

wherein R$^1$ is hydrogen or a straight, branched or cyclic alkyl group of 1 to 6 carbon atoms R$^2$ is an acyl or alkoxycarbonyl group of 1 to 15 carbon atoms in which some or all of the hydrogen atoms on the constituent carbon atoms may be substituted with halogen atoms, R$^3$ is an acid labile group, represented by

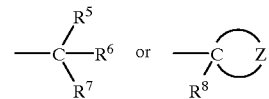

wherein R$^5$ to R$^8$ are independently selected from straight, branched or cyclic alkyl groups of 1 to 15 carbon atoms, the sum of carbon atoms in R$^5$, R$^6$ and R$^7$ is at least 5, and Z is a divalent hydrocarbon group of 4 to 15 carbon atoms which form a ring with the carbon atom to which it is connected at opposite ends, k is 0 or 1, and m is an integer from 0 to 5.

14. The ester compound of claim 13 having the following general formula (2) or (3):

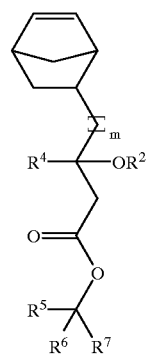

(2)

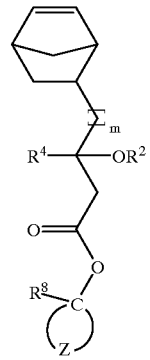

(3)

wherein m and R$^2$ are as defined above, R$^4$ is hydrogen or methyl, R$^5$ to R$^8$ are independently selected from straight, branch or cyclic alkyl groups of 1 to 15 carbon atoms, the sum of carbon atoms in R$^5$, R$^6$ and R$^7$ is at least 5, and Z is a divalent hydrocarbon group of 4 to 15 carbon atoms which forms a ring with the carbon atom to which it is connected at opposite ends.

15. A method of preparing the ester compound of claim 1, comprising the step of effecting addition reaction of a metal enolate of acetate of the following formula (5) to a carbonyl compound of the following formula (4) to form a β-hydroxyester compound of the following formula (6), and effecting acylation or alkoxycarbonylation of the hydroxyl group on the β-hydroxyester compound,
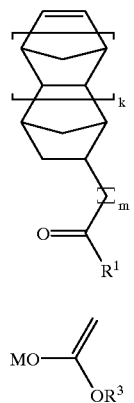
(4)
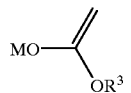
(5)
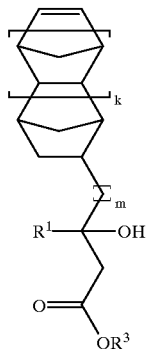
(6)
wherein k, m, $R^1$ and $R^3$ are as defined above, M is Li, Na, K MgY, or ZnY and Y is a halogen atom.
* * * * *